US009694095B2

(12) United States Patent
Paskalov

(10) Patent No.: US 9,694,095 B2
(45) Date of Patent: *Jul. 4, 2017

(54) PLASMA POWDER STERILIZATION APPARATUS AND METHODS

(71) Applicant: Applied Quantum Energy LLC, Gardena, CA (US)

(72) Inventor: George Paskalov, Torrance, CA (US)

(73) Assignee: APPLIED QUANTUM ENERGY LLC, Gardena, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/525,913

(22) Filed: Oct. 28, 2014

(65) Prior Publication Data
US 2015/0044095 A1 Feb. 12, 2015

Related U.S. Application Data

(63) Continuation of application No. 13/711,867, filed on Dec. 12, 2012, now Pat. No. 8,871,145.
(Continued)

(51) Int. Cl.
| A61L 2/00 | (2006.01) |
| A61L 2/14 | (2006.01) |
| A61L 2/20 | (2006.01) |
| A23L 3/005 | (2006.01) |
| A23B 4/015 | (2006.01) |
| A23L 3/26 | (2006.01) |

(52) U.S. Cl.
CPC ............... *A61L 2/14* (2013.01); *A23B 4/015* (2013.01); *A23L 3/005* (2013.01); *A23L 3/26* (2013.01); *A61L 2/20* (2013.01)

(58) Field of Classification Search
CPC ............ A61L 2/14; A23B 4/015; A23L 3/005
USPC .......................................... 422/22
See application file for complete search history.

(56) References Cited

U.S. PATENT DOCUMENTS

| 4,046,527 A | 9/1977 | Kistemaker |
| 4,133,638 A | 1/1979 | Healey |
(Continued)

FOREIGN PATENT DOCUMENTS

| WO | 01/12350 | 2/2001 |
| WO | 2010/142953 | 12/2010 |
| WO | 2011/035104 | 3/2011 |

OTHER PUBLICATIONS

Fujiwara, K. et al., "The Sterilization of Dry Powdered Foods by Successive Impacts", Materials Science Forum, vol. 556, pp. 191-196, 2008.
(Continued)

*Primary Examiner* — Kevin Joyner
(74) *Attorney, Agent, or Firm* — Fish & Tsang, LLP

(57) ABSTRACT

Systems and methods for plasma sterilization are described. The sterilization method includes placing a substance to be sterilized in a rotating chamber (e.g., drum) and exposing the substance to a radio frequency (RF) plasma. The mixing of the substance and plasma is further promoted by generating a magnetic field that produces a force on the substance in a direction opposite to the rotational direction of the chamber. In other aspects, the chamber may have a gas permeable wall. In addition, the substance may be exposed to acoustic shock waves produced by a modulating RF generator.

17 Claims, 2 Drawing Sheets

Related U.S. Application Data

(60) Provisional application No. 61/718,493, filed on Oct. 25, 2012, provisional application No. 61/569,485, filed on Dec. 12, 2011, provisional application No. 61/569,449, filed on Dec. 12, 2011.

(56) References Cited

U.S. PATENT DOCUMENTS

| | | | |
|---|---|---|---|
| 4,207,286 | A | 6/1980 | Gut Boucher |
| 4,676,195 | A | 6/1987 | Yasui et al. |
| 4,756,882 | A | 7/1988 | Jacobs et al. |
| 5,588,357 | A | 12/1996 | Tomikawa et al. |
| 6,543,460 | B1 * | 4/2003 | Denes ............... A01C 1/00 134/1.1 |
| 2006/0147648 | A1 | 7/2006 | De Vries et al. |
| 2007/0000381 | A1 | 1/2007 | Larouche et al. |
| 2008/0317626 | A1 | 12/2008 | Arnold et al. |
| 2010/0044483 | A1 | 2/2010 | Foret |
| 2010/0254853 | A1 | 10/2010 | Lee et al. |
| 2012/0145041 | A1 | 6/2012 | Walters |

OTHER PUBLICATIONS

Kim, W. et al., "Flame Stabilization Enhancement and NOx Production using Ultra Short Repetitively Pulsed Plasma Discharges", 44th AIAA Aerospace Sciences Meeting and Exhibits, Jan. 9-12, 2006, Reno, Nevada.

* cited by examiner

PLASMA POWDER STERILIZATION APPARATUS AND METHODS

This application is a continuation of U.S. patent application Ser. No. 13/711,867, now U.S. Patent No. 8,871,145 filed Dec. 12, 2012 which claims the benefit of priority to U.S. Provisional Patent Application No. 61/718,493 filed on Oct. 25, 2012, U.S. Provisional Patent Application No. 61/569,485 filed on Dec. 12, 2011, and U.S. Provisional Patent Application No. 61/569,449 filed on Dec. 12, 2011. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is plasma sterilization.

BACKGROUND

The following description includes information that may be useful in understanding the present invention. It is not an admission that any of the information provided herein is prior art or relevant to the presently claimed invention, or that any publication specifically or implicitly referenced is prior art.

While numerous sterilization processes and devices are known, most are not well suited for sterilizing food powder and other food-based materials. This is due, in part, to the fact that food material is sensitive and easily damaged (e.g., its composition can be easily changed).

For example, while the medical industry frequently utilizes high pressure and/or high temperature vessels (e.g., autoclaves) to sterilize medical instruments, sterilizing food material in this manner would substantially alter the composition of the food material.

Other industries, such as the pharmaceutical industry, utilize radiation-based sterilization rather than high pressure/temperature sterilization processes to avoid damaging or altering highly sensitive pharmaceutical formulations. Unfortunately, radiation-based sterilization processes may also damage food material.

Other industries use shock wave sterilization processes to sterilize matter without producing excessive heat. See, for example, PCT/US2010/049248 and U.S. Pat. No. 5,588,357. Unfortunately, high shock pressures can also degrade food material.

U.S. Pat. No. 4,756,882 (Jacobs) describes a sterilization process in which objects are contacted with hydrogen peroxide, and trace amounts of residual hydrogen peroxide are subjected to plasma treatment to generate an active species. The active species are effective to kill microbes. Any residual hydrogen peroxide simply converts into non-toxic decomposition products. This sterilization process may be used with food material.

While the plasma sterilization process described in Jacobs can be used to sterilize food materials, the systems and devices described in Jacobs are intended for batch processing, and are therefore not well suited to sterilizing large volumes of food material.

Thus, there is still a need for improvements in plasma sterilization devices and methods.

SUMMARY OF THE INVENTION

The inventive subject matter provides apparatus, systems and methods in which a substance to be sterilized is placed in a rotating chamber (e.g., drum) and irradiated with a radio frequency (RF) plasma. Mixing of the substance and the plasma is further promoted by generating a magnetic field that produces a force on the substance in a direction opposite to the rotational direction of the chamber.

In one aspect of some embodiments, the magnetic field is produced by a DC power supply and a magnetic system. The DC power supply could be configured to provide both the radial plasma current and the magnetic field. In other aspects of some embodiments, the magnetic field may be axially aligned with the chamber. In yet other aspects, an induction plasma may be used to pre-ionize the plasma.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
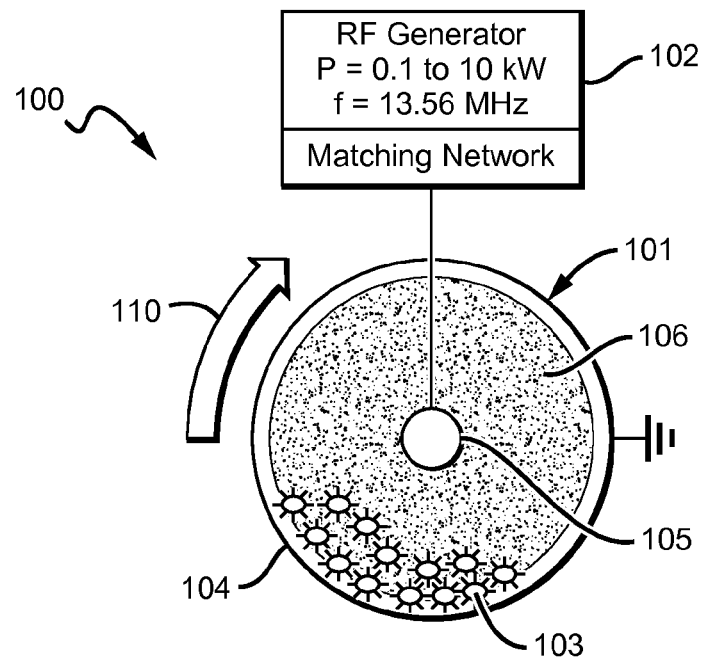
FIG. 1 is a drawing of one embodiment of a sterilization system.

FIG. 1 shows a sterilization system 100 comprising a drum 101 and an RF generator 102. A substance 103 is placed inside the internal chamber of drum 101. Substance 103 can be any material that a user desires to sterilize. In some embodiments, substance 103 is a food material (e.g., food powder). The outer wall of drum 101 serves as an external RF electrode 104. Inside drum 101 is a internal RF electrode 105. As drum 101 rotates in direction 110, RF generator 102, electrode 104, and electrode 105 operate to produce RF plasma 106 inside the chamber of drum 101. RF plasma 106 can be an ionized gas such as air (e.g., $O_2$, $CO_2$, $N_2$, Ar). RF plasma 106 contains an active species that is effective to kill microbes in substance. (Further discussion of plasma sterilization processes is found in the background section of U.S. Pat. No. 4,756,882, which is incorporated herein by reference.)

In some embodiments, RF generator 102 operates at or near 13.56 MHz, with power in the range of 0.1 to 10 kW.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Figure 2:
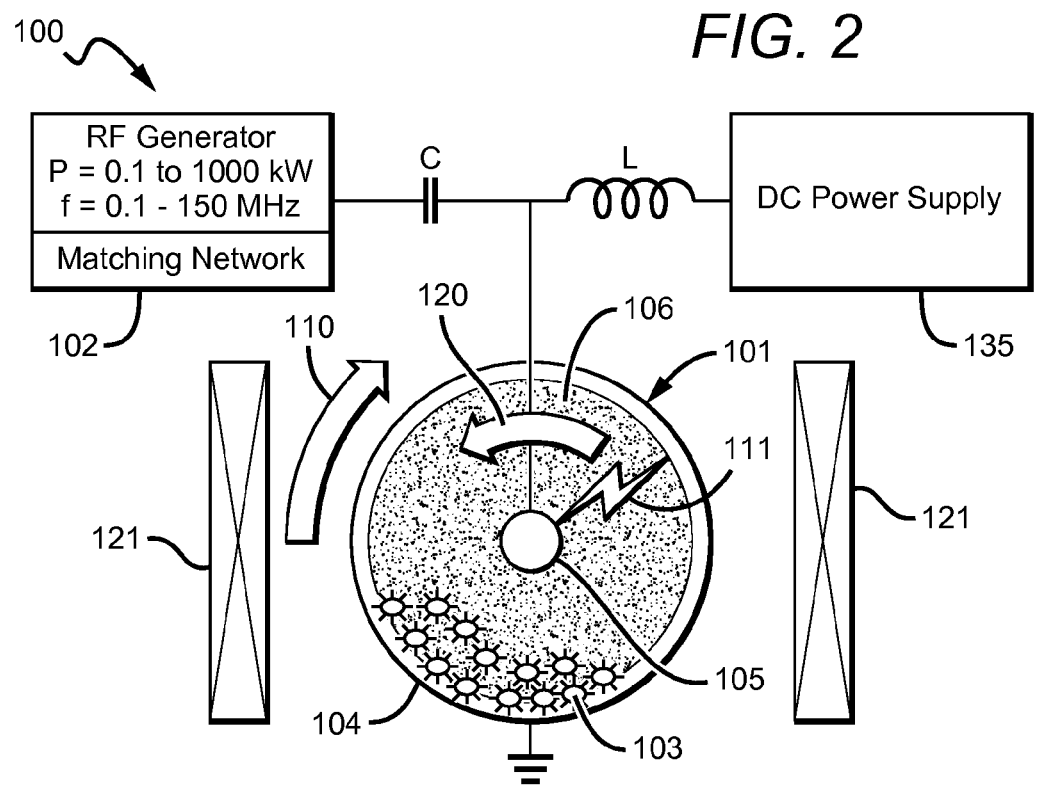
FIG. 2 is a drawing of the sterilization system of FIG. 1, disposed in a magnetic field.

FIG. 2 shows system 100 in relation to a magnetic field 121, which produces a plasma rotation direction 120. The fundamental principles of the influence of magnetic field 121 will now be explained.

A Lorentz force is the force on a point charge due to electromagnetic fields. It is given by the following equation in terms of the electric and magnetic fields:

$$F=q[E+(v \times B)]$$

Where, F is the force, E is the electric field, B is the magnetic field (e.g., magnetic field 121), q is the electric charge of the particle, v is the instantaneous velocity of the particle, x is the vector cross product. A positively charged particle in plasma will be accelerated in the same linear orientation as the E field, but will curve perpendicularly to both the instantaneous velocity vector v and the B field according to the right-hand rule.

RF plasma 106 will have a rotation direction opposite to rotation 110 of drum 101. As a result, the contact time between RF plasma 106 and substance 103 is much higher and the sterilizing effect is much higher. In addition, interactions between RF plasma 106 and substance 103 are more efficient.

Figure 3:
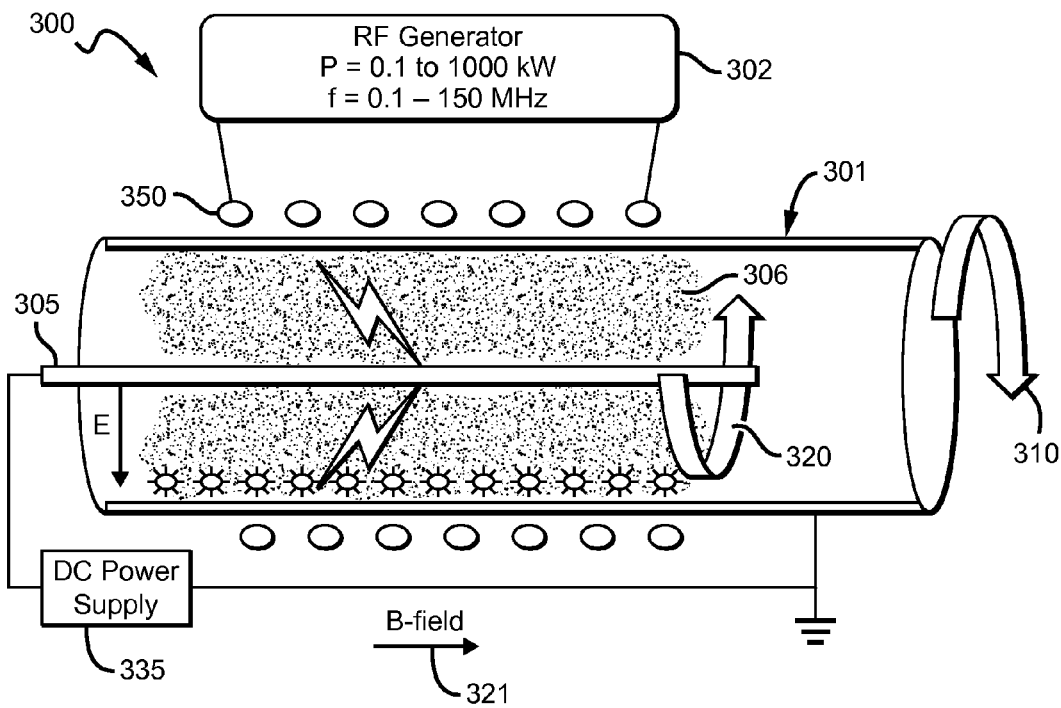
FIG. 3 is a drawing of another embodiment of a sterilization system.

FIG. 3 shows another embodiment, sterilization system 300, in which an induction plasma is used as a pre-ionizer for the main RF plasma by using an external inductive coil 350. In this scenario, the RF plasma 306 inside the internal chamber of reactor 301 is more uniform. Internal electrode 305 is connected only to DC power supply 335 in order to generate radial current and rotate the plasma in direction 320 by using Lorentz force produced from magnetic field 321.

Figure 4:
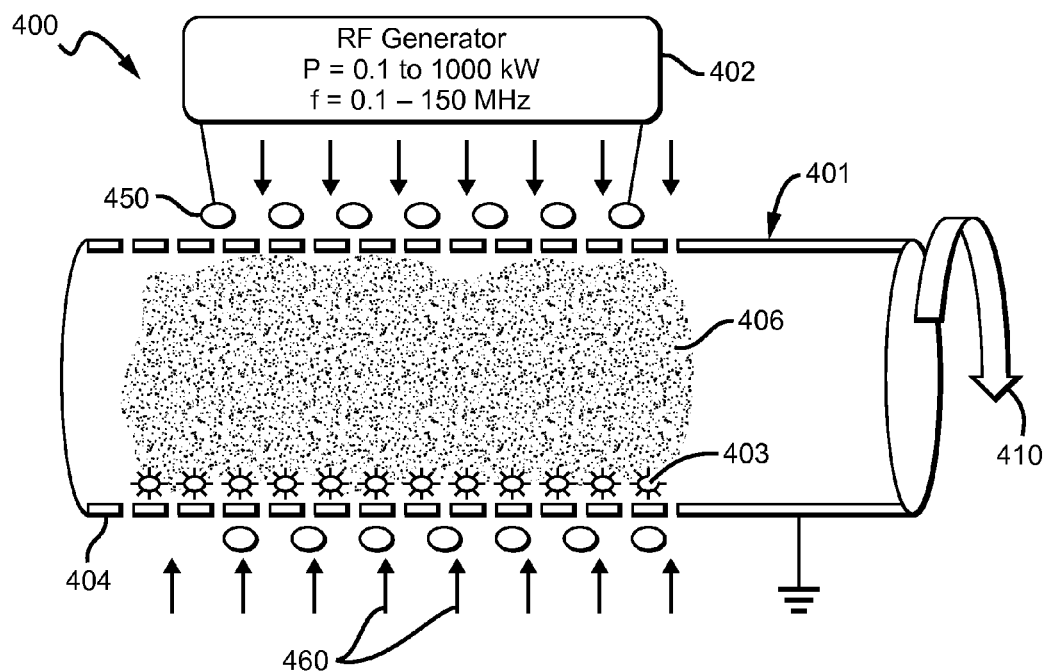
FIG. 4 illustrates another embodiment of a sterilization system.

FIG. 4 shows yet another alternative embodiment, sterilization system 400, which has an RF plasma 406 produced by RF generator 402. Unlike previous embodiments, reactor 401 has a porous wall (i.e., external electrode 404 is porous). The porous wall can be made of porous stainless steel or some other porous conductive material. The plasma gas is supplied to reactor 401 through the porous wall, which keeps powder 403 (e.g., the substance to be sterilized) from directly contacting the reactor's wall. RF plasma 406 will be much more uniform (especially at higher pressure) than when plasma gas is supplied from an end of the reactor.

In addition to the inventive concepts described above, plasma sterilization processes can utilize plasma to generate and precisely control shock waves. For example, the plasma generating frequency (basic frequency) could be 13.56 MHz, but modulated in order to produce the shock/acoustic waves. In this scenario, the plasma is just a "body", which could oscillate at any frequency and power. The acoustic/ultrasound is transmitted through a medium via pressure waves by inducing vibrational motion of the molecules, which alternately compress and stretch the molecular structure of the medium due to a time-varying pressure.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of sterilizing a substance, comprising:
   placing the substance in a rotating chamber;
   producing a plasma inside the rotating chamber;
   applying a magnetic field to the plasma inside the rotating chamber to produce a plasma rotation direction that is opposite to the rotational direction of the rotating chamber to increase mixing of the substance and active species.

2. The method of claim 1, wherein the substance is a food powder.

3. The method of claim 2, wherein the plasma has an active species that is effective to kill microbes in the food powder.

4. The method of claim 1, wherein the step of producing a plasma inside the rotating chamber comprises operating an RF generator.

5. The method of claim 4, wherein an outer wall of the rotating chamber serves as an external RF electrode.

6. The method of claim 5, wherein the rotating chamber has an internal RF electrode.

7. The method of claim 6, wherein the RF generator, external RF electrode, and internal RF electrode operate to produce plasma inside the rotating chamber.

8. A method of sterilizing a substance, comprising:
placing the substance in a rotating chamber;
supplying a plasma to the inside of the rotating chamber;
applying a magnetic field to the plasma inside the rotating chamber to produce a plasma rotation direction that is opposite to the rotational direction of the rotating chamber to increase mixing of the substance and active species.

9. The method of claim 8, wherein the step of supplying a plasma to the inside of the rotating chamber comprises operating an inductive coil.

10. The method of claim 9, wherein the inductive coil is wound around the outside of the rotating chamber.

11. The method of claim 8, wherein the rotating chamber has a porous wall.

12. The method of claim 11, wherein the step of supplying a plasma to the inside of the rotating chamber comprises introducing the plasma into the rotating chamber through the porous wall.

13. The method of claim 12, wherein the porous wall is made of a conductive material.

14. The method of claim 12, wherein the porous wall is made of stainless steel.

15. The method of claim 12, wherein the porous wall comprises an external RF electrode.

16. The method of claim 11, wherein the step of supplying a plasma to the inside of the rotating chamber comprises introducing the plasma into the rotating chamber from an end of the chamber.

17. The method of claim 8, further comprising the step of keeping the substance from directly contacting the wall of the rotating chamber.

* * * * *